(12) United States Patent
Ingenhoven et al.

(10) Patent No.: US 6,530,755 B2
(45) Date of Patent: Mar. 11, 2003

(54) MICROPUMP

(75) Inventors: Nikolaus Ingenhoven, Männedorf (CH); Noa Schmid, Grabs (CH); Stefano Fornito, Gossau (CH); Werner Hälg, Männedorf (CH)

(73) Assignee: Tecan Trading AG, Männedorf (CH)

( * ) Notice: Subject to any disclaimer, the term of this patent is extended or adjusted under 35 U.S.C. 154(b) by 0 days.

(21) Appl. No.: 09/817,309

(22) Filed: Mar. 26, 2001

(65) Prior Publication Data

US 2001/0028854 A1 Oct. 11, 2001

(30) Foreign Application Priority Data

Apr. 7, 2000 (CH) ................................................ 0692/00

(51) Int. Cl.$^7$ ............................................... F04B 17/00
(52) U.S. Cl. ................... 417/413.1; 417/322; 417/415; 60/20
(58) Field of Search .............................. 417/322, 413.1, 417/413.2, 413.3, 415; 604/20, 153

(56) References Cited

U.S. PATENT DOCUMENTS

| 4,052,320 A | | 10/1977 | Jakubowicz |
| 4,389,657 A | * | 6/1983 | McMahon ............... 346/140 R |
| 4,553,059 A | * | 11/1985 | Abe et al. ................... 310/328 |
| 4,615,360 A | | 10/1986 | Jacobs |
| 5,094,594 A | | 3/1992 | Brennan |
| 6,033,191 A | * | 3/2000 | Kamper et al. ............. 417/322 |
| 6,179,584 B1 | * | 1/2001 | Howitz et al. .............. 417/413 |

FOREIGN PATENT DOCUMENTS

| DE | 29708678 | | 8/1997 | ........... F04B/43/04 |
| EP | 0725267 | | 8/1996 | ........... G01N/1/00 |
| JP | 09232227 A | * | 9/1997 | |
| WO | 98/26179 | | 6/1998 | ........... F04B/43/04 |

OTHER PUBLICATIONS

Fred K. Forster, 1997, University of Washington, Seattle, Micro–Pumps With No–Moving–Part Valves, 15 pages.*
Zheng Cui, 2002, Rutherford Appleton Laboratory, UK, A Knowledge BAse for Microfluidic Devices, 14 pages.*

* cited by examiner

*Primary Examiner*—Charles G. Freay
*Assistant Examiner*—John F Belena
(74) *Attorney, Agent, or Firm*—Notaro & Michalos, P.C.

(57) ABSTRACT

The ejection orifice (7) of a micropump including a baseplate (3) of glass and a cover plate (4) of silicon and intended for ejecting small liquid drops, has a diameter of about 50 μm, and is located in the center of a flat front surface (12) which, in order to avoid accumulations of liquid in the region of the ejection orifice (7), is only 8 times the area thereof and, along a continuous circular edge, is adjacent a lateral surface (13) in the form of an envelope of truncated cone. The front surface (12) and the lateral surface (13) have a surface roughness of not more than N4 and are provided, for example, with a hydrophobic plasma polymer coating.

10 Claims, 2 Drawing Sheets

MICROPUMP

FIELD OF THE INVENTION

The invention relates to a micropump as used especially for the delivery of small liquid drops from the air in laboratory apparatuses for chemical, in particular biochemical and medical investigations.

PRIOR ART

In the case of known micropumps of the generic type by means of which liquid drops are delivered from the air, the ejection orifice is usually located eccentrically in a larger, substantially flat, generally rectangular surface. Although EP 0 725 267 A2 proposed making the tip of a micropump pyramidal, no further information is given and it is to be assumed that it is actually intended to form a truncated pyramid in the relatively large flat front surface of which the ejection orifice is eccentrically located.

However, it has been found that a larger front surface surrounding the ejection orifice has a disadvantageous effect on the reliability of the ejection of the liquid drops and on the reproducibility of the drop size. This is due in particular to the fact that an accumulation of liquid concentrated around the ejection orifice readily forms on the front surface and influences the drop ejection in an uncontrollable manner and in certain circumstances even prevents said ejection.

SUMMARY OF THE INVENTION

It is the object of the invention to provide a micropump of the generic type in which the ejection of liquid drops takes place with high reliability and little variation of the drop size.

This object is achieved by the features in the claimed invention. The accumulation of liquid in the vicinity of the ejection orifice is as a rule avoided. However, even if such an accumulation of liquid nevertheless forms—for example because regulation of the liquid feed is not very precise—said accumulation remains slight and does not reach a troublesome amount since the liquid flows away laterally. The ejection of liquid drops thus takes place undisturbed and the drop size depends only on the properties of the liquid, on the size of the ejection orifice and on the control of the actuator.

BRIEF DESCRIPTION OF THE DRAWINGS

The invention is explained in more detail below with reference to Figures which show only an embodiment and wherein:

FIG. 2b is a bottom view of that part of the micropump which is shown in FIG. 2a;

FIG. 3b is a bottom view of the tip shown in FIG. 3a; and

DESCRIPTION OF THE PREFERRED EMBODIMENTS

Figure 1:
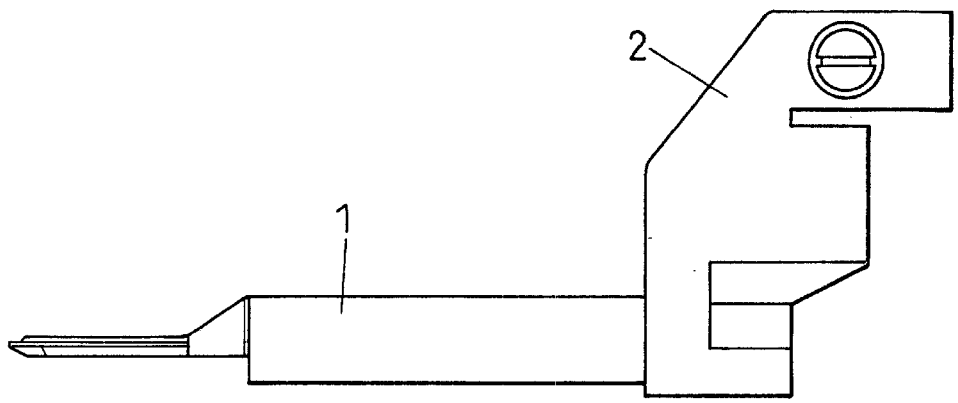
FIG. 1 is a side view of a micropump according to the invention in a holder.
Figure 2A:
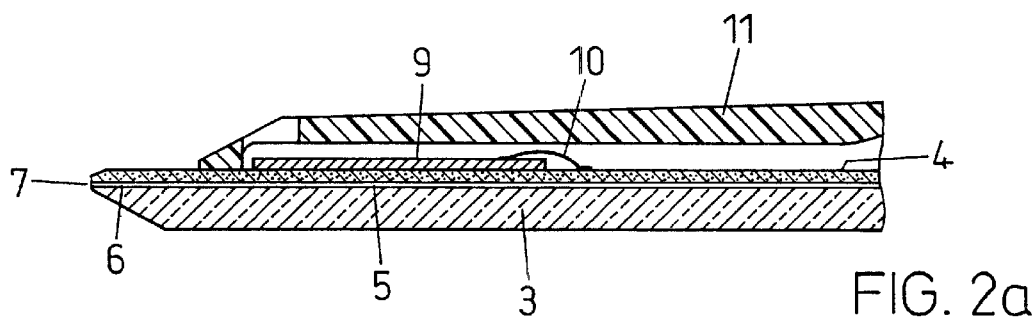
FIG. 2a is a longitudinal section through the front part of the micropump of FIG. 1 on a larger scale.
Figure 2B:
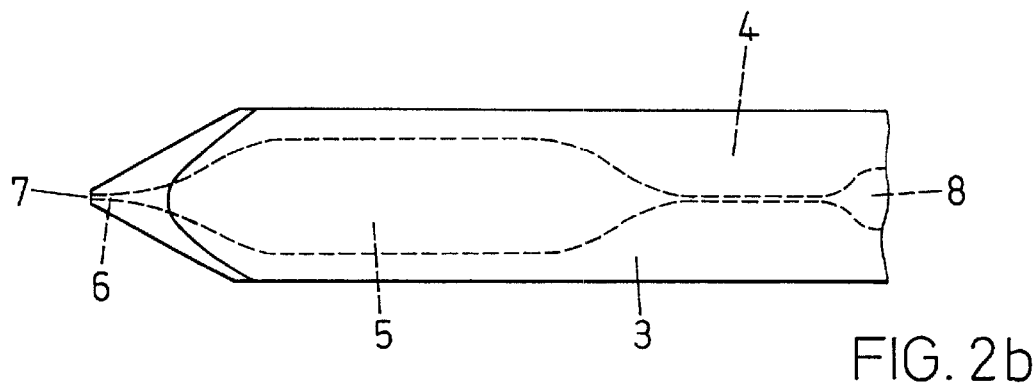

FIG. 1 shows a micropump 1 according to the invention in a holder 2 which can be suspended, for example, in a three-dimensionally movable mount of a micropipetting apparatus. The micropump 1 has (FIG. 2a,b) a baseplate 3 of glass, e.g. boron glass, having a flat top which is connected to the bottom of a thinner cover plate 4 of silicon. A pump chamber 5 about 50 μm high and a straight ejection channel 6 of the same height connected to said chamber at the front and tapering to a segment of constant cross-section which ends in an ejection orifice 7 are etched from the otherwise likewise flat bottom of the cover plate 4. An inflow channel 8 which ends in an inflow orifice (not shown) which can be connected to a storage vessel or a pump, e.g. a dilutor, is connected via a constriction to the opposite end of the pump chamber 5. A plate-like piezoelectric element 9 which is controlled via lines 10 is mounted as an actuator on a part of the top of the cover plate 4 which is opposite the pump chamber 5. The piezoelectric element 9 and the major part of the cover plate 4 are protected by a cover 11. As shown in FIG. 2a, it may be in the form of a plastics cover or may consist of a casting material—preferably of plastic—with which the piezoelectric element 9 and the lines 10 are embedded.

Figure 3A:
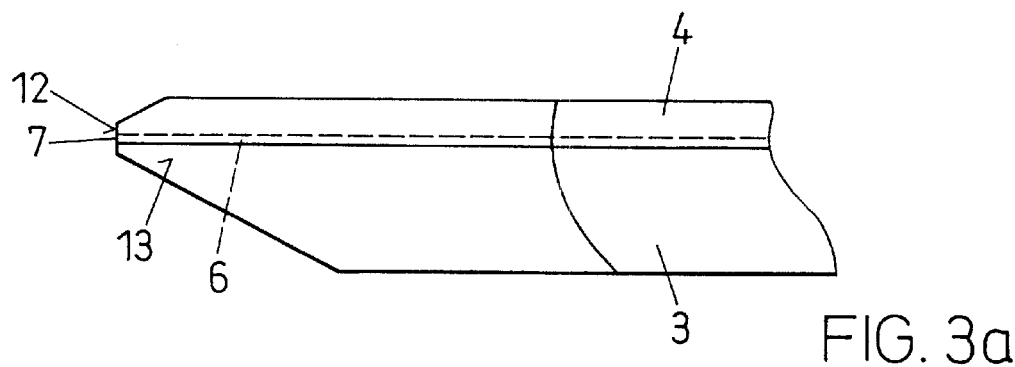
FIG. 3a is, once again on a larger scale, a side view of the tip of that front part of the micropump which is shown in FIG. 2a,b.
Figure 3B:
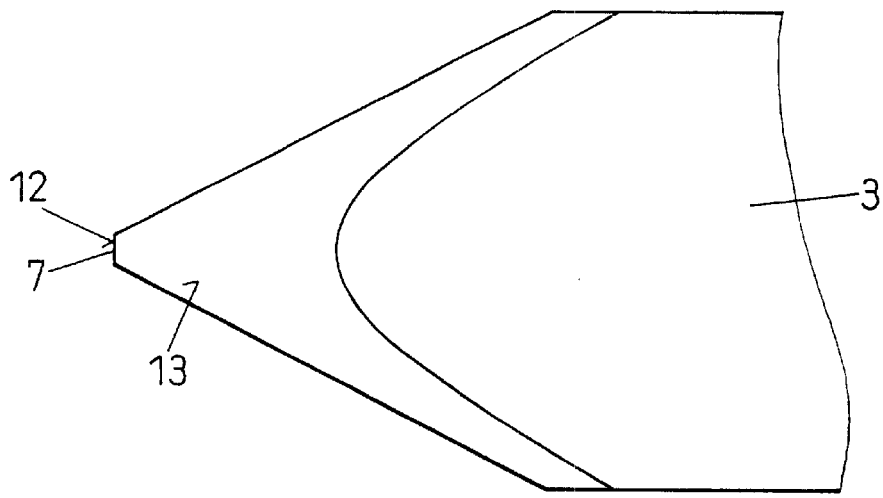
Figure 4:
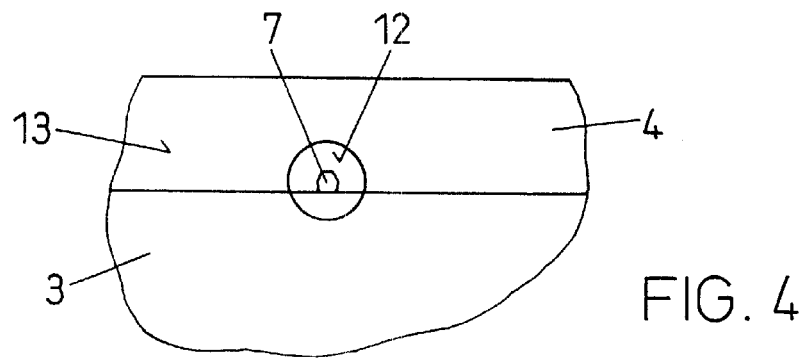
FIG. 4 is, once again on a larger scale, a front view of the tip shown in FIG. 3a,b.

The ejection orifice 7 is (FIGS. 3a,b, 4) approximately circular. It is surrounded concentrically by a flat annular front surface 12. A lateral surface 13 which is rotationally symmetrical, in particular in the form of an envelope of truncated cone, and concentric with the front surface 12 is adjacent to the edge bounding the outside of the front surface 12. The diameter of the ejection orifice 7 is about 50 μm and that of the front surface 12 is about 150 μm. The area of the front surface 12 is thus about 8 times the area of the ejection orifice 7. It has been found that, with such ratios, no troublesome accumulations of liquid can form on the front surface 12.

The smaller the area ratio, the more advantageous in principle are the properties of the micropump with regard to the avoidance of troublesome accumulations of liquid in the region of the ejection orifice. The lower limit for the diameter of the front surface is determined by manufacturing tolerances and requirements with respect to robustness. Micropumps which can be produced without a great deal of expense are those having front surfaces of about 200 μm to about 250 μm in diameter, which, assuming a diameter of about 50 μm for the ejection orifice, leads to area ratios of about 1:15 to 1:25. A diameter of 150 μm for the front surface, as stated above, can also readily be realized. In most circumstances, the properties of the micropump are well within the permitted ranges even with very much larger area ratios than those stated above. The limit is about 1:250, which corresponds approximately to a diameter of 750 μm for the front surface, and is of course dependent on other parameters and on the requirements with respect to the function of the micropump.

The angle between the axis and the generator of the lateral surface 13 is about 30°. It should as far as possible not be larger than 60° so that if necessary liquid flows away from the front surface over its outer edge onto the lateral surface to a sufficient extent. It has been found that the described formation of the lateral surface is also suitable for avoiding the formation of accumulations of liquid on the front surface on withdrawal of the tip of the micropump from a liquid level if said tip is used, for example, as a pipette tip and is occasionally also immersed for drawing up liquid, for example by means of a downstream pump.

Slight roughness of the surface on the front surface 12 and at least one adjacent region of the lateral surface 13, which as far as possible should be N4 or less, is also advantageous for avoiding accumulations of liquid in the region of the ejection orifice 7. Said roughness can be reduced by a suitable coating which, owing to its chemical composition, can also reduce the adhesion of liquid. It can be hydrophobic or hydrophilic, depending on the properties of the liquid. In the case of micropumps for the delivery of aqueous liquids, for example, a hydrophobic plasma polymer coating has proved advantageous.

The micropump according to the invention is produced substantially in a manner known per se, by connecting a rectangular silicon plate, from which the pump chamber, the ejection channel and the inflow channel have been etched, by anodic bonding to a glass plate which is likewise rectangular. The lateral surface 13 is then created by grinding by means of a diamond grinding disc, and the tip of the micropump is thus completed. The piezoelectric element 9 and the electrical lines 10 to said element, and the cover 11, are then mounted. Finally, the front surface 12 and also at least part of the lateral surface 13 are coated.

The delivery of liquid drops by means of the micropump takes place as in known micropumps of the generic type, in such a way that the cover plate 4 is bent abruptly downwards of the piezoelectric element 9. The reduction in the f the pump chamber 5 causes a pressure wave which runs the ejection channel 6 to the outlet orifice 7 and liquid drop to be ejected from said orifice.

LIST OF REFERENCE SYMBOLS

1 micropump
2 holder
3 baseplate
4 cover plate
5 pump chamber
6 ejection channel
7 ejection orifice
8 inflow channel
9 piezoelectric element
10 lines
11 cover
12 front surface
13 lateral surface

What is claimed is:

1. A micropump comprising:
   a pump chamber having a length and a width area, whose volume can be reduced by an actuator;
   a pipette tip or a dispense tip;
   an ejector channel which leads from the pump chamber to an ejection orifice of the pipette or dispense tip which is surrounded by a front surface; and
   the front surface of the pipette or dispensing tip forming a substantially flat area with a substantially circular outer edge, said flat area being not more than 250 times the area of the ejection orifice of the pipette or dispense tip and being bounded by an edge of a lateral surface surrounding said flat area, and wherein said lateral surface is substantially rotation symmetrical.

2. The micro pump of claim 1, wherein the ejection orifice is concentrically surrounded by said front surface, said front surface being a flat annular front surface and the lateral surface being in the form of an envelope of a truncated cone.

3. The micropump of claim 1, including a baseplate of glass and a silicon cover plate, the pump chamber, ejection and inflow channels having the same height and being etched from the otherwise likewise flat bottom of the silicon cover plate connected to the glass base plate having a flat top, wherein this silicon cover plate is thinner than the glass plate.

4. The micropump of claim 3, the actuator being a plate shaped piezoelectric element, and wherein the actuator is mounted on the flat top of the silicon cover opposite the pump chamber.

5. The micropump of claim 1, the lateral surface being defined by an axis and a generator, and wherein the angle between the axis and the generator of the lateral surface is lass than 60°.

6. The micropump of claim 5, wherein the angle between the axis and the generation of the lateral surface is less than 30°.

7. The micropump of claim 1, wherein the diameter of the front surface is less than 750 $\mu$m.

8. The micropump of claim 7, wherein the diameter of the front surface is less than 250 $\mu$m.

9. The micropump of claim 1, wherein the front surface and at least a directly adjacent marginal region of the lateral surface has a roughness of equal or better than N4 and/or is provided with a hydrophic or hydrophilic coating.

10. Micropump (1) comprising a pump chamber (5), whose volume can be reduced by means of an actuator, and an ejection channel (6) which leads from the pump chamber (5) to an outlet orifice (7) surrounding by a front surface (12), the front surface (12) forming a substantially flat surface which is bound by an edge of a lateral surface (13) surrounding it and whose area is not more that 250 times the area of the ejection orifice (7), the front surface (12) have a roughness of not more than N4 and so does at least one directly adjacent marginal region of the lateral surface (13).

* * * * *